US00PP28191P3

(12) United States Plant Patent
Suphachadiwong

(10) Patent No.: US PP28,191 P3
(45) Date of Patent: Jul. 11, 2017

(54) *SANSEVIERIA* HYBRID PLANT NAMED 'SUPSAN1402'

(50) Latin Name: ***Sansevieria* Thunb.**
Varietal Denomination: Supsan1402

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 117 days.

(21) Appl. No.: 14/757,005

(22) Filed: Nov. 6, 2015

(65) Prior Publication Data

US 2016/0143206 P1 May 19, 2016

(30) Foreign Application Priority Data

Nov. 14, 2014 (QZ) ..... PBR 2014/2946

(51) Int. Cl.
*A01H 5/12* (2006.01)

(52) U.S. Cl.
USPC ..... Plt./382

(58) Field of Classification Search
USPC ..... Plt./373, 382
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Sansevieria* cultivar named 'Supsan1402' which is characterized by the combination of pineapple-like foliage with a limited number of arched leaves radiating from a basal rosette, unique coloration and patterning of the foliage, narrow foliage, soft and brittle foliage which will not inflict bodily harm, and the stability of all characteristics from generation to generation. The new variety is a *Sansevieria,* typically produced as an indoor ornamental plant.

2 Drawing Sheets

Latin name of the genus and species: The Latin name of the genus and species of the novel variety disclosed herein is *Sansevieria* Thunb.

Variety denomination: The inventive variety of *Sansevieria* disclosed herein has been given the variety denomination 'Supsan1402'.

CROSS REFERENCE TO RELATED APPLICATIONS

This application claims priority to the Community Plant Variety Rights application number 2014/2946, filed Nov. 14, 2014, which is herein incorporated by reference.

BACKGROUND OF THE INVENTION

Parentage: The *Sansevieria* variety 'Supsan1402' originated as a seedling selection from the controlled pollination of the unpatented, proprietary seed parent, *Sansevieria* hybrid 'VH5', with the unpatented, proprietary pollen parent, *Sansevieria* 'MH5'. Both parents were developed by, and are owned by, the inventor and were never commercially released. Said crossing was conducted by the inventor in a small, netted greenhouse in Chonburi, Thailand in December of 2010. Seeds resulting from the cross were harvested and subsequently sown in March of 2011. Resulting progeny were grown to maturity for the evaluation of unique characteristics. Of these progeny, several varieties were selected which exhibited a pineapple-like growth habit with a limited number of arched leaves radiating from a basal rosette, unique coloration and patterning of the foliage, and foliage which was soft and brittle so as not to inflict injury if the plants were to come into contact with a hand or other body part.

After further observation of said candidate varieties, one plant was selected in March of 2012 which exhibited a combination of unique characteristics suitable for commercial release. After identifying the new variety as a potentially interesting selection, the inventor continued confidential testing and propagation, assessing stability of the unique characteristics of this variety. The new cultivar was given the breeder denomination 'Supsan1402'.

Asexual Reproduction: Asexual reproduction of 'Supsan1402' by way of harvesting vegetative ground shoots was first initiated in April of 2012 at Chonburi, Thailand. Access to all plants was restricted, as plants were kept in a greenhouse not open to the public. Through subsequent propagation of vegetative ground shoots, eight generations have been reproduced, which have shown that the unique features of this cultivar are stable and reproduced true to type.

SUMMARY OF THE INVENTION

The cultivar 'Supsan1402' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'Supsan1402'. These characteristics in combination distinguish 'Supsan1402' as a new and distinct *Sansevieria* cultivar:

1. *Sansevieria* 'Supsan1402' exhibits a limited number of leaves; and
2. *Sansevieria* 'Supsan1402' exhibits a pineapple-like growth habit with a limited number of arched leaves radiating from a basal rosette; and
3. *Sansevieria* 'Supsan1402' exhibits foliage with a unique color pattern of dark green and silver; and,
4. *Sansevieria* 'Supsan1402' exhibits narrow foliage; and
5. *Sansevieria* 'Supsan1402' exhibits soft and brittle foliage which will not inflict bodily harm if plants come into contact with a hand or other body part.

BOTANICAL DESCRIPTION OF THE PLANT

Figure 1:
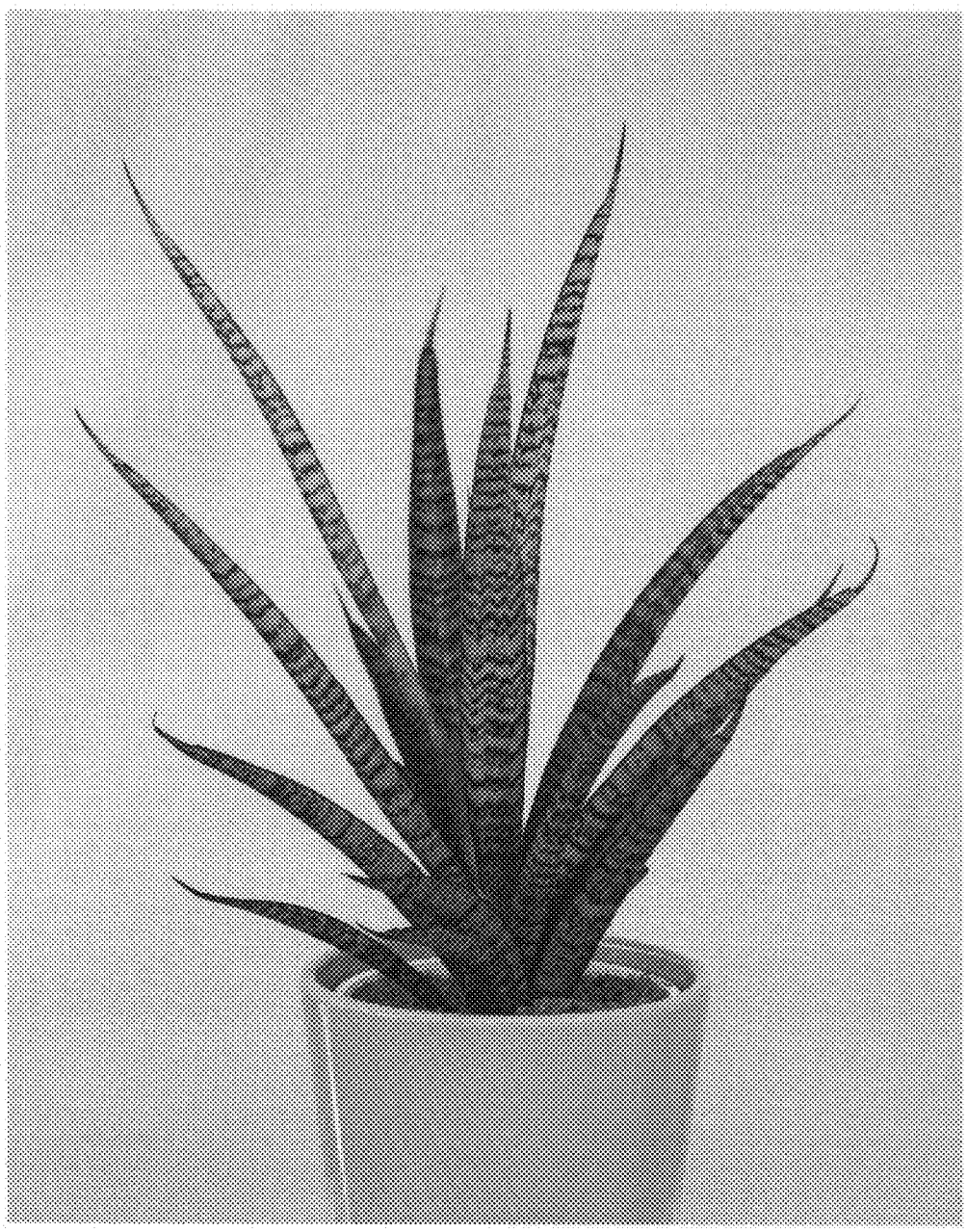
FIG. 1 illustrates, as nearly true as it is reasonably possible to make the same in color photographs of this type, an exemplary plant of 'Supsan1402' grown in a grown in a commercial greenhouse in Chonburi, Thailand. This plant is approximately 20 weeks old, shown planted in a 10.5 cm container.
Figure 2:
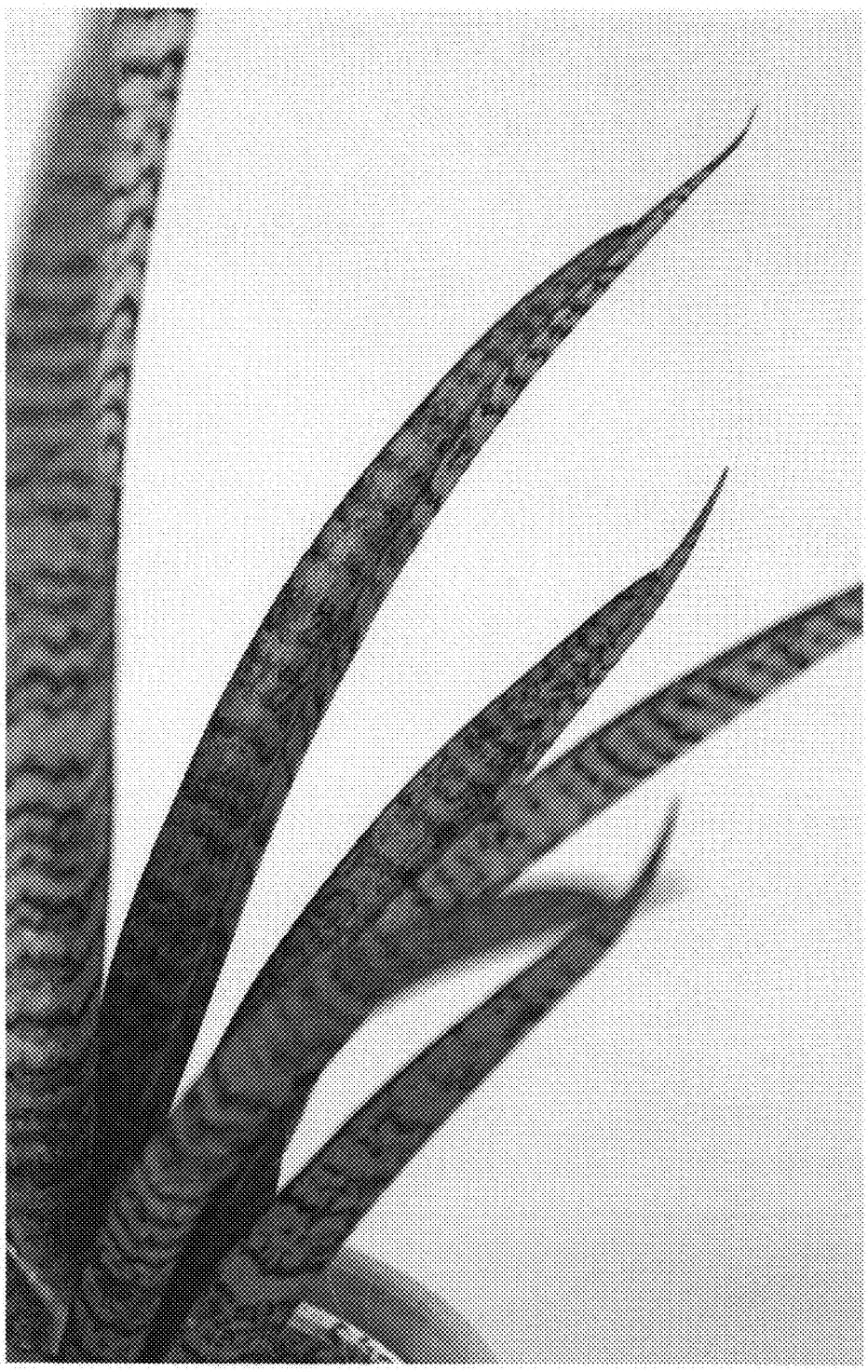
FIG. 2 illustrates, as nearly true as it is reasonably possible to make the same in color photographs of this type, the typical foliage of 'Supsan1402'.

The following observations and measurements describe a twenty week-old 'Supsan1402' plant grown in a commercial greenhouse in Chonburi, Thailand. The plants were grown under plastic with a 20% shade cloth, thus controlling the amount of sunlight and sheltering said plants from rain.

Those skilled in the art will appreciate that certain characteristics will vary with older or, conversely, with younger plants. 'Supsan1402' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'Supsan1402' and comparisons with other varieties of *Sansevieria* are provided below.

Plant description:

*Growth habit.*—Monopodial; rosulate.

*Average height.*—30.3 cm.

*Plant spread.*—Average of 31.1 cm.

*Growth rate.*—Approximately 5 cm per month.

*Propagation type.*—Division of vegetative ground shoots; harvesting ground shoots from the mother plant.

*Propagation details.*—The time needed to root a shoot division is approximately 2 to 3 months with temperatures ranging from approximately 14 to 40 degrees Celsius.

*Disease resistance.*—Similar to other *Sansevieria* varieties.

*Drought tolerance and cold tolerance.*—Similar to other *Sansevieria* varieties.

Root system:

*General.*—Moderately dense and moderately branched rooting; roots are moderately thick to slightly fibrous.

*Texture.*—Slightly fleshy.

*Color.*—Greyed-Orange RHS N170B.

Foliage:

*Arrangement.*—Rosulate.

*Abundance; density.*—18 leaves on a 20 week-old plant.

*Lamina.*—Dimensions — 24.1 cm long (including the leaf sheath) and 2.1 cm wide. Thickness — Approximately 0.6 cm. Shape of blade — Linear; strongly carinate and succulent. Aspect — Leaves are arched and emerge from the soil at an average angle of 65° to soil level (with 0° being horizontal). Apex — Pungent yet not sharp to the touch. Base — Decurrent. Margin — Entire. Texture of top surface — Glabrous, moderately glossy. Texture of bottom surface — Glabrous, moderately glossy. Color — Juvenile foliage, adaxial surface — Green, in between near RHS 137B and 137C; radially banded and marbled with Yellow-Green near RHS 147D to Greyed-Green near RHS 193A. Juvenile foliage, abaxial surface — Green near RHS 137B; radially banded and marbled with Yellow-Green RHS 148D to Greyed-Green RHS 194B. Mature foliage, adaxial surface — Green, in between RHS 139A and N189A, yet darker; strongly radially banded and marbled with Green near RHS 137B and 137C. Mature foliage, abaxial surface — Green, near RHS 139A; strongly radially banded and marbled with Yellow-Green RHS 148D to Greyed-Green RHS 191B. Venation — Parallel. Venation Coloration — Not distinguishable from the leaf surface; coloration is the same as surrounding leaf.

*Petiole.*—No petioles present, leaves sessile.

*Sheath.*—Dimensions — 2.8 cm long and 1.8 cm wide, on average. Color — Yellow-Green, near RHS 145C to 145D. Texture — Glabrous; moderately glossy.

Inflorescence: No flowering has been observed to date.

COMPARISONS WITH THE PARENT PLANTS

Plants of the new cultivar 'Supsan1402' are similar to the seed parent, *Sansevieria* 'VH5', in most horticultural characteristics. However 'Supsan1402' differs from the seed parent in the following characteristics:

1. 'Supsan1402' exhibits a larger overall plant size when compared to 'VH5'.
2. The foliage color of 'Supsan1402' is more attractive when compared to the foliage color of 'VH5'.
3. When compared to 'Supsan1402', 'VH5' exhibits more vigorous growth and a greater number of shoots per plant, in plants of equivalent age.

Plants of the new cultivar 'Supsan1402' are similar to the pollen parent, *Sansevieria* 'MH5', in most horticultural characteristics. However 'Supsan1402' differs from the pollen parent in the following characteristics:

1. 'Supsan1402' exhibits a more compact growth habit and a smaller overall plant size when compared to 'MH5'.
2. 'Supsan1402' exhibits a more distinct patterning of the foliage color when compared to the foliage patterning of 'MH5'.
3. When compared to 'Supsan1402', 'MH5' exhibits more vigorous growth and a greater number of shoots per plant, in plants of equivalent age.

COMPARISONS WITH SIMILAR *SANSEVIERIA* CULTIVARS KNOWN TO THE INVENTOR

'Supsan1402' is similar in many horticultural characteristics to the commercial variety *Sansevieria* 'Farah' (unpatented in the United States). However 'Supsan1402' differs from 'Farah' in the following characteristics:

1. The primary foliage color of 'Supsan1402' is dark green, whereas the primary foliage color of 'Farah' is a lighter green color.
2. The secondary foliage color of 'Supsan1402' is silver, whereas 'Farah' almost completely lacks a secondary foliage color.
3. The abaxial foliage color of 'Supsan1402' is silver and green, whereas the abaxial foliage color of 'Farah' is green.
4. 'Supsan1402' exhibits thicker foliage when compared to the foliage of 'Farah'.
5. 'Supsan1402' exhibits wider foliage when compared to the foliage of 'Farah'.
6. The foliage of 'Supsan1402' is more arched when compared to the upright foliage of 'Farah'.
7. 'Supsan1402' produces fewer ground shoot offsets and is therefore less dense, when compared to 'Farah'.

That which is claimed is:

1. A new and distinct variety of *Sansevieria* plant named 'Supsan1402', substantially as described and illustrated herein.

* * * * *